United States Patent
Matsuzawa et al.

(10) Patent No.: US 7,074,756 B2
(45) Date of Patent: Jul. 11, 2006

(54) LIVER GENERATION PROMOTER

(75) Inventors: Yuji Matsuzawa, Takarazuka (JP); Tohru Funahashi, Suita (JP); Shinji Tamura, Mino (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 10/479,581

(22) PCT Filed: Jun. 5, 2002

(86) PCT No.: PCT/JP02/05574

§ 371 (c)(1),
(2), (4) Date: Dec. 3, 2003

(87) PCT Pub. No.: WO02/100427

PCT Pub. Date: Dec. 19, 2002

(65) Prior Publication Data

US 2004/0180818 A1    Sep. 16, 2004

(30) Foreign Application Priority Data

Jun. 7, 2001    (JP)    ............................. 2001-172882

(51) Int. Cl.
*A61K 38/00*    (2006.01)
(52) U.S. Cl. ............................. 514/2; 514/12
(58) Field of Classification Search .................... 435/6; 424/457–470; 536/23.5; 514/12
See application file for complete search history.

(56) References Cited

FOREIGN PATENT DOCUMENTS

| JP | 2000-256208 | 9/2000 |
|---|---|---|
| JP | 2000-336040 | 12/2000 |
| WO | 02/072149 | 9/2002 |

OTHER PUBLICATIONS

Y. Arita et al., "Paradoxical Decrease of an Adipose-Specific Protein, Adiponectin, in Obesity", Biochemical and Biophysical Research Communications, vol. 257, 1999, pp. 79-83.*
S. Kihara, "Adiponectin", Hormon & Clinic, Apr. 1, 2001, vol. 49, No. 4, pp. 9-15, with full English translation.

Y. Matsuzawa et al., "Molecular mechanism of Metabolic syndrome X: contribution of adipocytokines adipocyte-derived bioactive substances", Annals of the New York Academy of Sciences, vol. 892, 1999, pp. 146-154.
T. Yokota et al., "Adiponectin, a new member of the family of soluble defense collagens, negatively regulates the growth of myelomonocytic progenitors and the functions of macrophages", Blood, vol. 96, No. 5, 2000, pp. 1723-1732.
M. Yoda-Murakami et al., "Change in expression of GBP28/ adioponectin in carbon tetrachloride-administrated mouse liver", Biochemical and Biophysical Research Communications, vol. 285, No. 2, Jul. 13, 2001, pp. 372-377.
K. Maeda et al., "cDNA Cloning and Expression of a Novel Adipose Specific Collagen-like Factor, apM1 (Adipose Most Abundant Gene Transceipt 1)", Biochemical and Biophysical, Research Communications, vol. 221, 1996, pp. 286-289.
Y. Artia et al., "Paradoxical Decrease of an Adipose-Specific Protein, Adiponectin, in Obesity", Biochemical and Biophysical Research Communications, vol. 257, pp. 79-83, (1999).
Kihara et al., "Anti-atherogenic property of adipocyte-derived plasma protein, adiponectin". BIOSIS, 2001, XP00297211, abstract.
Ouchi et al., "Adipocyte-derived plasma protein, adiponectin, suppresses lipid accumulation and class A scavenger receptor expression in human monocyte-derived macrophages", Circulation, American Heart Association, Texas, U.S. vol. 103, No. 8, pp. 1057-1063. Feb. 2001, XP002970251.
N. Kihara, "Adiponectin, Hormone to Rinsho", Apr. 1, 2001, vol. 49, No. 4, pp. 9-15.

* cited by examiner

*Primary Examiner*—Jon Weber
*Assistant Examiner*—Marsha Tsay
(74) *Attorney, Agent, or Firm*—Wenderoth, Lind & Ponack, L.L.P.

(57) ABSTRACT

Although it is known that adiponectin, which is adipose-specific protein, has effects of suppressing the proliferation and migration of vascular smooth muscle, an effect against arteriosclerosis, an effect of inhibiting the activation of monocytes and macrophages and an anti-inflammatory effect, its action on hepatic stellate cells has never been known hitherto. The present invention has elucidated that adiponectin inhibits the actions of TGFB and PDGF on hepatic stellate cells and thereby exerts effects of suppressing hepatic fibrosis and promoting the proliferation of normal hepatocytes.

2 Claims, 3 Drawing Sheets

LIVER GENERATION PROMOTER

This application is a U.S. national stage of International Application No. PCT/JP02/05574 filed Jun. 5, 2002.

TECHNICAL FIELD

The present invention relates to a liver regeneration promoting agent comprising adiponectin, a liver regeneration promoting method by administering adiponectin to a patient and use of adiponectin for producing a liver regeneration promoting agent.

BACKGROUND ART

It is well known that liver is an organ having an extremely high ability of regenerating itself. However, in a case of chronic hepatic disease, liver undergoes fibrosis during the process of the liver regeneration after continuous necrosis of hepatocytes, resulting in suppressing normal hepatocyte regeneration. This may be assumed to be due to a reduced sinusoidal blood flow resulting from an increase in an extracellular matrix involved in hepatic fibrosis, and also due to loss of space for the liver regeneration resulting from the occupation by the fibers produced.

The production of an extracellular matrix involved in hepatic fibrosis takes place mainly in an activated HSC (hepatic stellate cell). When the HSC is activated by cytokines such as TGF (transforming growth factor)-β or PDGF (platelet derived growth factor) produced by platelet Kupffer cells and the like, or activated by oxidation stress, it expresses α-smooth muscle actin (αSMA) and acquires smooth muscle cell property, whereby transforming into a myofibroblast-like cell. In addition, activated HSC exhibits an excessive expression of TGFβ receptor and the production of the extracellular matrix protein is promoted by an autocrine mechanism. The TGFβ also has a hepatocyte proliferation inhibiting effect.

Accordingly, we considered that if the action of the TGFβ and PDGF on the HSC could be suppressed by any method, it might lead to suppression of the hepatic fibrosis and serve to normalize the liver regeneration after hepatic disorder.

An objective of the invention is to provide a medicament which suppresses the hepatic fibrosis, promotes the liver regeneration and normalizes the liver.

Adiponectin is an animal adipose tissue-specific protein separated newly from human adipose tissue by Maeda et al in 1996, and its amino acid sequence is also known (Maeda K, et al. Biochem. Biophys. Res. Commun. 221: 286 (1996)).

Almost at the same time, other researchers identified a substance named ACRP30 cloned from mouse 3T3-F 442A cells (Scherer P E et al., J. Biol. Chem. 270: 26746–26749 (1995)), which is believed to be identical to adiponectin.

This adiponectin is abundantly present not only in an adipose tissue but also in blood. In normal human blood it is present at a level as high as 5 to 10 μg/ml (Arita Y et al., Biochem. Biophys. Res. Commun. 257: 79–83 (1999)).

Paradoxically, the blood level of this adiponectin is reduced as obesity advance.

The effect of the adiponectin was not elucidated entirely, although some researchers reported that it had a vascular smooth muscle proliferation on suppressing effect, a cell migration suppressing effect, an anti-arteriosclerotic effect, a suppressive effect on the activation of monocyte and macrophage, an anti-inflammatory effect and the like.

DISCLOSURE OF THE INVENTION

We investigated extensively other action of the adiponectin and finally discovered that the adiponectin has actions which were not known so far, such as a hepatic stellate cell activation suppressive effect, an extracellular matrix production suppressive effect, a hepatic stellate cell proliferation suppressive effect, a liver regeneration promoting effect and the like. Based on such findings, we made a further effort and established the invention.

Thus, the present invention relates to:

(1) a liver regeneration promoting agent comprising adiponectin, especially a preventive or therapeutic agent against liver cirrhosis or a preventive or therapeutic agent against chronic hepatitis;

(2) a method for promoting liver regeneration comprising administering an effective amount of adiponectin to a patient in need thereof, especially a method for preventing or treating liver cirrhosis or a method for preventing or treating chronic hepatitis; and, (3) use of adiponectin for producing a liver regeneration promoting agent, especially, a preventive or therapeutic agent against liver cirrhosis or a preventive or therapeutic agent against chronic hepatitis.

As already mentioned, the adiponectin is a protein which is produced in adipose tissue of an animal including human and which is abundantly present also in blood.

Human adiponectin has been obtained as a highly purified substance by a gene recombination method from a cDNA encoding it (Arita, Y et al., Biochem. Biophys. Res. Commun. 257, 79–83 (1999)). Mouse-derived ACRP 30 is obtained as a highly purified substance by gene recombination techniques as described in the reference described above and is also available.

A patient to which an inventive liver regeneration promoting agent is administered is a patient whose liver is undergoing or at a risk of fibrosis due to chronic liver disease, especially chronic hepatitis. By administering an effective amount of the inventive liver regeneration promoting agent to such a patient, the fibrosis can be inhibited or prevented and the regeneration of normal hepatocytes is promoted.

A liver regeneration promoting agent of this invention can be administered systemically or locally to a patient in need thereof. A systemic administration may for example be a parenteral administration such as an intravenous injection, subcutaneous injection, intramuscular injection and the like, an oral administration. The gene therapy is also applicable.

The dosage form of a medicament according to the present invention may for example be a liquid formulation such as an injection formulation, as well as a solid formulation such as a powder, granule, tablet, capsule, suppository and the like.

A pharmaceutical preparation to be given parenterally to a human may for example be an injection formulation and a suppository. When the pharmaceutical preparation is formulated as an injection formulation, those which may be employed are solvents (distilled water for injection and the like), stabilizers (sodium edetate and the like), osmotic agents (sodium chloride, glycerin, mannitol and the like), pH modifiers (hydrochloric acid, citric acid, sodium hydroxide and the like), suspending agents (methyl cellulose, sodium carboxymethyl cellulose and the like), while a suppository base (cocoa butter, Macrogol and the like may appropriately be selected and employed when it is formulated as a suppository.

The dosage forms for oral administration to human may for example be a powder, granule, tablet, capsule, syrup and liquid formulation. When a pharmaceutical preparation is formulated as a powder, granule, tablet and the like, appropriate pharmaceutical carriers for a solid formulation such as excipients (starch, corn starch, glucose, fructose, sugar and the like), lubricants (magnesium stearate), disintegrants (starch, crystalline cellulose, binders (starch, gum arabic and the like) may be employed, and the formulation may be coated with an appropriate coating (gelatin, sugar, gum arabic, carnauba wax and the like), enteric coating (cellulose acetate phthalate, methacrylic acid copolymer, hydroxypropyl cellulose phthalate, carboxymethyl ethyl cellulose and the like). As a coating for a sustained release formulation (drug delivery system (DDS) formulation), those which may be mentioned are hydroxypropylmethyl cellulose, ethyl cellulose, hydroxymethyl cellulose, hydroxypropyl cellulose, polyoxyethylene glycol, Tween 80, Pluronic F68, cellulose acetate phthalate, hydroxypropylmethyl cellulose phthalate, hydroxymethyl cellulose acetate succinate, Eudragit (Rohm, Germany, copolymer of methacrylic acid and acrylic acid) and the like. For formulating a capsule, an appropriate excipient, including those for improving the fluidity and the lubrication such as magnesium stearate, calcium stearate, talc, light silicic anhydride and the like, those for obtaining a fluidity under pressure such as crystalline cellulose and lactose as well as disintegrants mentioned above are added and mixed uniformly to form a particle with or without any suitable coating which is then filled in a capsule, or encapsulated using a capsule base having an increased plasticity obtained by supplementing a suitable capsule base (such as gelatin) with glycerin sorbitol or the like. Such a capsule may be supplemented if desired with colorants, preservatives [sulfur dioxide, parabenes (methyl, ethyl or propyl paraoxybenzoate) and the like]. The capsule may be an ordinary capsule or enteric coated capsule, gastric resistant capsule, controlled release capsule and the like. When formulating an enteric capsule, a liposome coated with an enteric coating may be filled in an ordinary capsule, or the capsule itself may be coated with an enteric coating, or may be molded using an enteric polymer as a base. When the composition is formulated as syrup or a liquid formulation, those which may be selected and employed appropriately are stabilizers (sodium edetate and the like), suspending agents (gum arabic, carmellose and the like), seasonings (simple syrup, glucose and the like) and flavors.

While the dose may vary depending on the type of the disease, sex and age of the patient, degree of the disease, administration mode and route and the like, it may be given for example via an intravenous injection to an adult suffering from liver cirrhosis at a daily dose of 1 to 100 mg/kg, preferably 3 to 20 mg/kg.

BEST MODE FOR CARRYING OUT THE INVENTION

The invention is further described in the following EXPERIMENTS and EXAMPLES.

EXPERIMENT 1

1. Materials and Methods

Separation of Rat Hepatic Stellate Cell (RHSC)

A male SD rat of 8 weeks old was anesthetized with Nembutal and subjected to laparotomy, and the portal vein was cannulated. The liver is digested first by the perfusion with $Ca^{2+}$ and $Mg^{2+}$-free Hanks solution followed by the perfusion with collagenase solution, and the hepatocytes were removed by centrifuging at a low speed and sieved through a mesh to obtain non-parenchymal cell suspension. Then the hepatic stellate cells were isolated using an elutriation rotor (3250 rpm/mm, 18 ml/min). The resultant stellate cells were seeded onto a plastic dish, subcultured by a trypsin/EDTA method, and the 3rd to 5th passages were employed in the following experiments.

The culture medium was DMEM medium supplemented with 10% FCS and 25 mg/l cefamedin and 30 mg/l kanamycin as antibiotics.

2. DNA Synthesis Suppressive Effect on RHSC

The DNA synthesis suppressive effect on RHSC was evaluated on the basis of $^3$H-thymidine incorporation of the cell.

That is, the RHSC after subcultured over 4 passages was seeded at $9 \times 10^3$ cells/well in a 96-well β plate. After verifying the adhesion of the cells on the following day, the cells were washed twice with PBS and incubated with serum-free medium. After 48 hours, stimulation with the adiponectin (ACRP30) at respective 0, 3, 10 and 30 μg/ml was conducted for 18 hours each in 6 wells containing the medium in the presence or absence of 10 ng/ml of PDGF. Subsequently, each well was pulsed with 1.0 μCi/ml $^3$H-thymidine for 5 hours and then the radioactivity was analyzed. The results are represented as counts per 30 seconds per well (FIG. 1).

Figure 1:
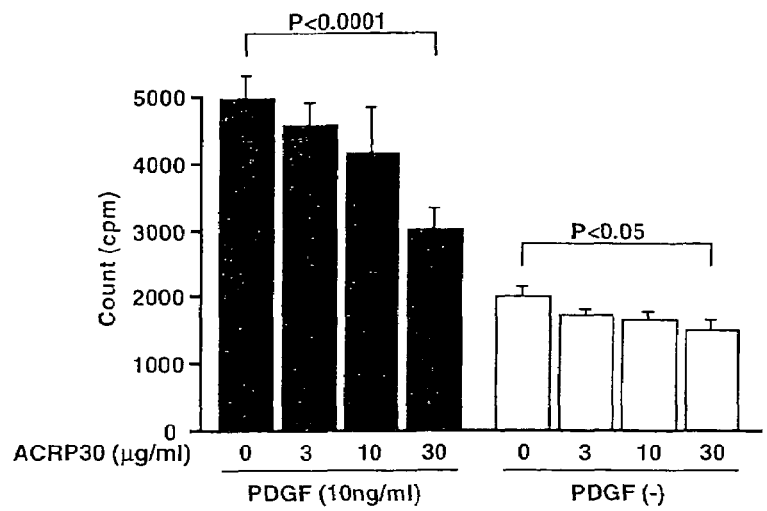
FIG. 1 shows a DNA synthesis suppressive effect of adiponectin (ACRP 30) on RHSC.

As evident from FIG. 1, the adiponectin suppressed the DNA synthesis by PDGF in a dose dependent manner.

3. RHSC Proliferation Suppressive Effect

The RHSC after subcultured over 4 passages was seeded at $2 \times 10^4$ cells/well in a 12-well β plate. After verifying the adhesion of the cells on the following day, the cells were washed twice with PBS and incubated with serum-free medium. After 48 hours, 10 ng/ml PDGF-supplemented adiponectin at 0, 10 and 30 μg/ml was added each to 3 wells whereby effecting the stimulation. On the 1st, 2nd, 4th and 6th days, the cells were harvested by a trypsin/EDTA method, and the number of cells was counted by a hemocytometer.

Figure 2:
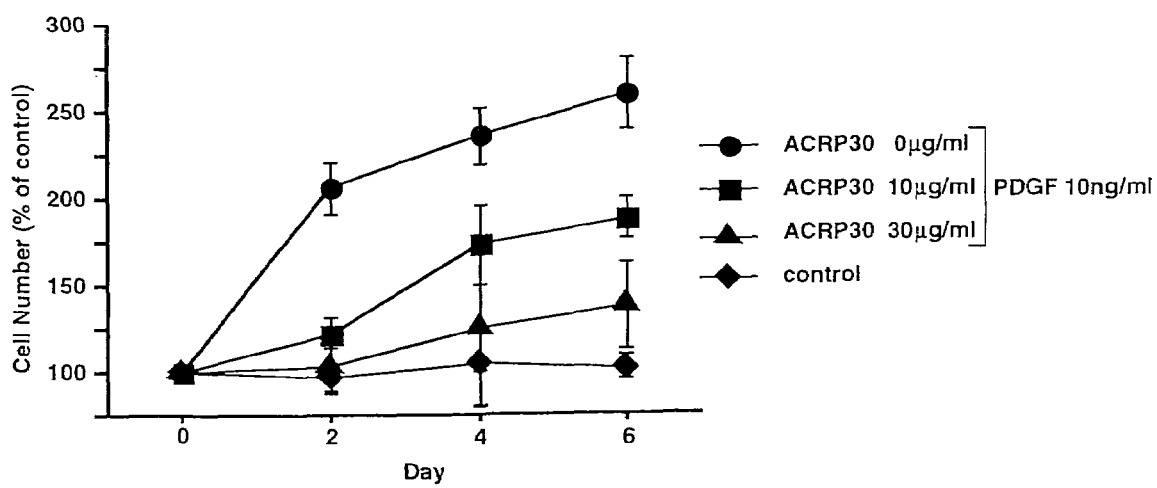
FIG. 2 shows a proliferation suppressive effect of adiponectin (ACRP 30) on RHSC.

The results are represented in FIG. 2 as percents based on the mean cell count on the day 0 as 100%.

As evident from FIG. 2, the adiponectin suppressed dose-dependently the proliferation of RHSC cell induced by PDGF.

4. Stellate Cell Migration Ability Suppressive Effect

The migrating ability was tested using a 24-well β plate and a cell culture insert whose pore size was 8 μm (Chemotaxicell, KURABO). A dish and a cell culture insert had previously been coated with type I collagen for 1 hour. After washing subconfluent RHSC twice with PBS using two dishes of 10 cm in diameter, the cells were incubated with serum-free medium for 48 hours. After washing twice with PBS, the cells were incubated for 30 minutes in the presence or absence of 30 µg/ml adiponectin, and then harvested by a trypsin/EDTA method. The cells were introduced into serum-free DMEM. The inserts were allowed to stand gently on a 24-well β plate containing various medium formulations. The formulations of the medium were all serum-free, and contained no adiponectin, or contained 10 ng/ml of PDGF and 30 µg/ml of adiponectin, and each was provided with 3 inserts. Each insert was seeded with $4 \times 10^4$ of RHSC. Subsequently, the cells were incubated at 37° C. for 5 hours and then the RHSC which emerged on the back of the insert were subjected to May-Giemsa staining and observed as magnified by 200 times to count the cells. The results are represented in FIG. 3 as percents based on the mean cell count in the control as 100%.

Figure 3:
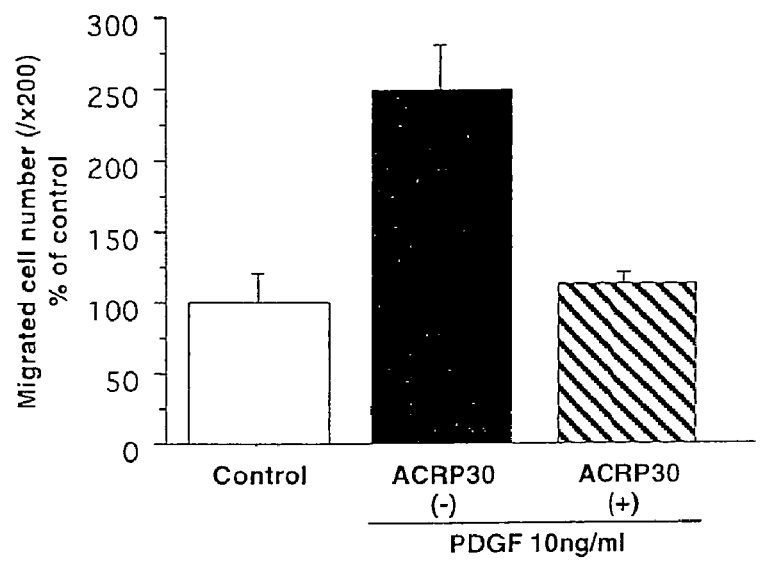
FIG. 3 shows a migration suppressive effect of adiponectin (ACRP 30) on RHSC.

As evident from FIG. 3, the adiponectin suppressed the migration of HSC to an extent almost similar to that in the control which was not stimulated by PDFG.

5. Effect of Adiponectin on TGFβ Stimulation

The RHSC was seeded in a 6-well β plate and washed at subconfluent twice with PBS, and incubated with serum-free DMEM. After incubating for 48 hours, the cells were cultured for 24 hours in various medium formulations including a control (TGFβ-free, adiponectin-free), 50 pg/ml TGFβ, 50 pg/ml TGFβ+30 µg/ml adiponectin. Subsequently, RNA was extracted from the RHSC in each well by Trizol method. The concentration of the RNA was measured by an spectro photometer, and each 1 µg was used as a template to prepare cDNA with RT (Reverse transcriptase). A 0.5 µl aliquot was used as a template to perform PCR. The PCR product was subjected to an electrophoresis on 1.5% agarose gel, and stained with Cyber Green. The PCR was conducted to the number of cycles which gave a linear amplification of each of the primers including TGFβ, TGFβ type II receptor or collagen Iα1 (25 cycles for TGFβ, 24 cycles for TGFβ type II receptor and 23 cycles for collagen Iα1). After running, the bands were scanned by an image scanner and inputted into a computer, where it was quantified by an Image Quant software.

A statistical analysis was conducted by the Kruskal-Wallis test for the comparison between groups and by the Scheffe test for the comparison between pairs. A statistically significant difference was defined as $P<0.05$.

Figure 4:
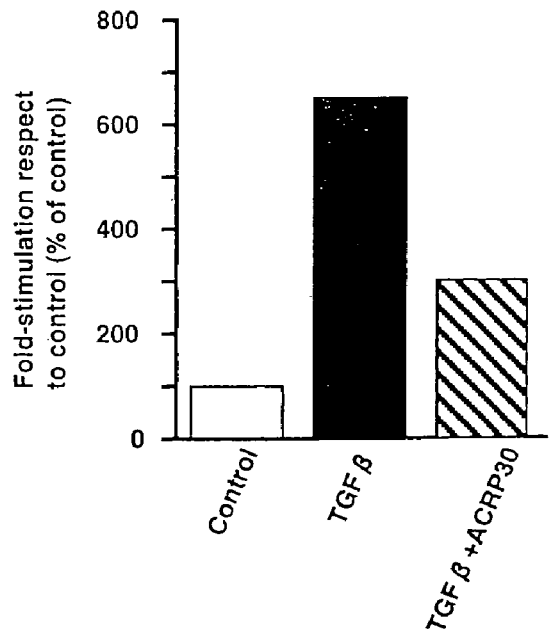
FIG. 4 shows a TGFβ mRNA expression suppressive effect of adiponectin (ACRP 30).
Figure 5:
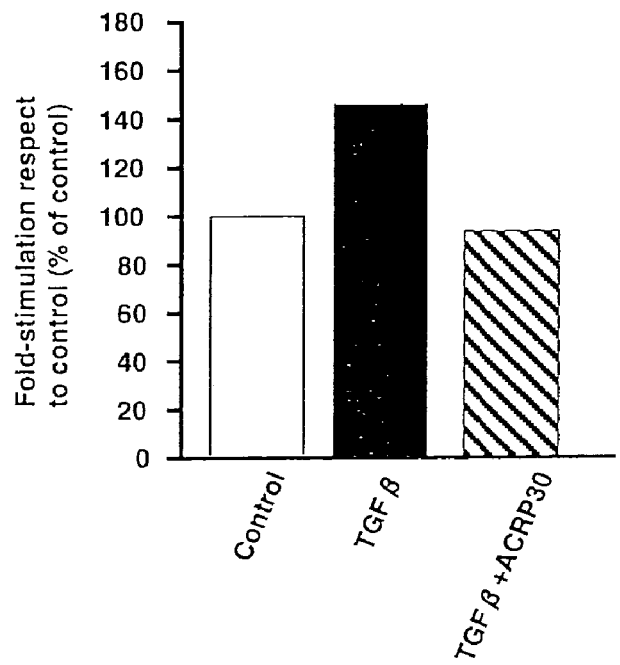
FIG. 5 shows a TGFβ type II receptor expression suppressive effect of adiponectin (ACRP 30).
Figure 6:
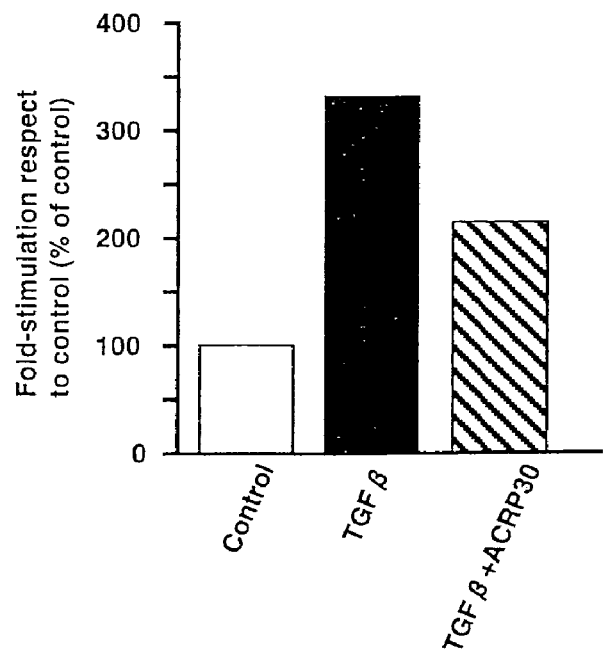
FIG. 6 shows a collagen Iα1 gene expression suppressive effect of adiponectin (ACRP 30).

As evident from FIG. 4, the adiponectin gave a marked suppression of the expression of TGFβ mRNA by the autocrine mechanism of TGFβ. As evident from FIG. 5, the TGFβ type II receptor expression was also suppressed. Accordingly, the adiponectin was proven to have a TGFβ signal suppressive effect. Also as evident from FIG. 6, the expression of collagen Iα1 gene whose expression is increased by TGFβ was also suppressed by the adiponectin.

EXAMPLE 1

Injection Formulation

| Adiponectin | 2 mg |
| Phosphate buffer (pH 7.0) | suitable amount |
| Total | 1 ml |

The above formulation was dispensed into 2 ml glass ampoules and sealed.

EXAMPLE 2

Tablet (Enteric Coating)

| Adiponectin | 0.8 g |
| Corn starch | 12 g |
| Lactose | 27.2 g |
| Magnesium stearate | 0.4 g |

The adiponectin, lactose and corn starch were combined and mixed thoroughly to obtain a granule for tablet compression in accordance with a wet tableting process. Magnesium stearate was added and the mixture was compressed into 400 tablets. Each tablet was coated with methacrylate copolymer for enteric coating.

Industrial Applicability

Since an inventive liver regeneration promoting agent suppresses an activated hepatic stellate cell-induced hepatic fibrosis and promotes normal hepatocyte regeneration and proliferation, it can promote the liver regeneration and normalize the hepatic functions when administered to a patient undergoing the hepatic fibrosis or at a risk of the hepatic fibrosis due for example to chronic hepatitis.

What is claimed is:

1. A method for promoting liver regeneration comprising administering an effective amount of adiponectin to a patient in need thereof.

2. A method for promoting liver regeneration according to claim 1 which is a method for inhibiting or treating liver fibrosis.

* * * * *